(12) United States Patent
Aonuma et al.

(10) Patent No.: US 6,906,814 B1
(45) Date of Patent: Jun. 14, 2005

(54) INTERFACING METHOD FOR NETWORK PRINTERS

(75) Inventors: Masashi Aonuma, Kanagawa-ken (JP); Masaaki Ohtsuka, Kanagawa-ken (JP); Takeshi Funahashi, Kanagawa-ken (JP)

(73) Assignee: Fuji Photo Film Co., Ltd., Kanagawa-ken (JP)

( * ) Notice: Subject to any disclaimer, the term of this patent is extended or adjusted under 35 U.S.C. 154(b) by 0 days.

(21) Appl. No.: 09/267,631

(22) Filed: Mar. 15, 1999

(30) Foreign Application Priority Data

| | | |
|---|---|---|
| Mar. 13, 1998 | (JP) | 10-063316 |
| Mar. 31, 1998 | (JP) | 10-087143 |
| Mar. 31, 1998 | (JP) | 10-087359 |

(51) Int. Cl.[7] .......... G06F 15/00; G06F 17/30
(52) U.S. Cl. ........... 358/1.15; 358/1.16; 358/1.14; 358/1.13; 707/3; 707/10
(58) Field of Search ............... 358/1.16, 1.15, 358/1.9, 1.1, 1.13, 1.14, 400, 448; 399/1, 8; 707/3, 10, 103

(56) References Cited

U.S. PATENT DOCUMENTS

| | | | | |
|---|---|---|---|---|
| 6,070,000 A | * | 5/2000 | Mori | 358/1.15 |
| 6,295,527 B1 | * | 9/2001 | McCormack et al. | 707/3 |
| 6,335,796 B1 | * | 1/2002 | Endo et al. | 358/1.15 |

* cited by examiner

Primary Examiner—Twyler Lamb
(74) Attorney, Agent, or Firm—Sughrue Mion, PLLC

(57) ABSTRACT

In an interfacing method, a plurality of network printers, which are provided with different kinds of film for image reproduction, are connected by an interface unit to an image information network. Available kinds of film with respect to each of the network printers, which are connected to the interface unit, are recognized. A network printer, which is among the plurality of the network printers and which corresponds to a kind of film coinciding with an output request, is selected in accordance with the results of the recognition. An output instruction, which coincides with the output request, is given to the thus selected network printer. An image can thereby be reproduced with the printer, which corresponds to the kind of film desired by an operator, such that considerable time and labor may not be required of the operator.

33 Claims, 7 Drawing Sheets

INTERFACING METHOD FOR NETWORK PRINTERS

BACKGROUND OF THE INVENTION

Field of the Invention

This invention relates to an interfacing method and an interface unit for network printers. This invention also relates to a client apparatus provided with functions of the interface unit for network printers. This invention further relates to a method and device for monitoring a network printer in a medical network, wherein a network printer designed to send a monitoring signal, which represents a state concerning output, in accordance with a special-purpose protocol may be connected to a plurality of terminals, each of which operates under management with one of plural kinds of operating systems having different forms. This invention still further relates to a method and system for managing a parameter wherein, in cases where a parameter, which represents image processing conditions, or the like, for a medical image to be reproduced by each of image output devices that reproduce medical images and are connected to a network, is altered in one of the image output devices, the details of the alteration are capable of being reflected in the other image output devices.

DESCRIPTION OF THE PRIOR ART

Various image forming systems (modalities) for diagnosis, in which X-rays, or the like, are utilized, have heretofore been used in the medical field. As such modalities, computed radiography (CR) systems, computed tomography (CT) systems, magnetic resonance imaging (MRI) systems, and the like, have been used in practice. An image having been formed by each modality is displayed on a cathode ray tube (CRT) display device or is reproduced on film by a laser printer (LP), or the like. The reproduced image is utilized for making a diagnosis, e.g. for investigating the presence or absence of a diseased part or an injury or for ascertaining the characteristics of the diseased part or the injury.

The CR systems are radiation image recording and read-out systems. With the radiation image recording and read-out systems, a radiation image of an object, such as a human body, is recorded on a sheet provided with a layer of a stimulable phosphor (hereinafter referred to as a stimulable phosphor sheet). The stimulable phosphor sheet, on which the radiation image has been stored, is then exposed to stimulating rays, such as a laser beam, which cause it to emit light in proportion to the amount of energy stored thereon during its exposure to the radiation. The light emitted by the stimulable phosphor sheet, upon stimulation thereof, is photoelectrically detected and converted into an electric image signal. Recently, the CR systems are widely used in practice. In cases where the CR system is connected to a network, which will be described later, it may be embodied as the entire radiation image recording and read-out apparatus described above or as a unit, such as a radiation image read-out apparatus, which is capable of feeding an ultimately detected image signal (image information) into the network.

With the rapid advances made in communication technology and computer technology in recent years, various kinds of networks utilizing computers have been built in hospitals. The aforesaid systems, which were used in the past stand-alone systems, constitute part of the network as image information input apparatuses. Also, CRT display devices and LP's are connected via an interface unit to the network and thereby constitute part of the network as image output devices.

In cases where LP's are connected to a network, the problems described below are encountered. Specifically, in cases where an image to be used in making a diagnosis is reproduced on film, it is necessary for sheets of film having various different sizes to be prepared in accordance with the desired image sizes. However, a single printer cannot necessarily carry out image reproduction on sheets of film having various different sizes. Also, sheets of film may be classified by base color into a colorless type, a blue type, and the like. Ordinarily, selection of a film base color is made according to preference of a medical doctor, who sees the image for diagnosis. However, if sheets of film having various different base colors are to be exchanged successively for image reproduction in a single printer, considerable time and labor will be required.

As described above, it is necessary for various different kinds of film (sizes, base colors, and the like) to be used in accordance with output requests. However, it is practically impossible that various different kinds of film are processed in a single printer.

Also, in cases where a malfunction occurs with a printer, image reproduction must wait before the repairing of the printer is finished.

Further, a printer is provided with a sorter for appropriately sorting the sheets of film, on which visible images have been reproduced, in accordance with output destinations (for example, destinations classified by department, such as destinations for surgical diagnosis, internal diagnosis, and dental diagnosis, and destinations classified by the kind of the object, the image of which was recorded). Ordinarily, sorter stages, which correspond to the number of sorting stages with the sorter, are approximately three to five stages per printer. However, in a network, various film output requests are made by many terminals, and therefore the sorting in a larger number of sorting stages is required. However, the number of the sorter stages cannot be increased unlimitedly due to limitation of physical space, which can be occupied by the sorter, at the location of the printer, and complexity of discharging paths from an output section of the printer to the sorter.

Therefore, it may be considered to connect a plurality of printers to a network. In such cases, it is necessary for an operator to specify a printer, which is to be used for reproducing an image on film, from one of terminals connected to the network.

However, ordinarily, the operator is a medical doctor, who desires to reproduce the image. In such cases, it is necessary for the medical doctor to memorize available kinds of film with respect to each of the printers and to specify a printer, with which image reproduction is to be carried out. Such a procedure is a burden to the medical doctor, who is the operator, and is not practicable.

Also, it is not practicable for the operator to grasp which printer is malfunctioning at present and to specify a normal printer.

Further, it is necessary for the operator to specify into which sorter stage of which printer the film should be sorted. Such a procedure is a burden to the operator and is not practicable.

SUMMARY OF THE INVENTION

The primary object of the present invention is to provide an interfacing method for printers, wherein an image is capable of being reproduced with a printer, which is among a plurality of printers connected to an image information network and which corresponds to a kind of film desired by an operator, such that considerable time and labor may not be required of the operator.

Another object of the present invention is to provide an interfacing method for printers, wherein an image is capable of being reproduced with a usable normal printer, which is among a plurality of printers connected to an image information network, such that considerable time and labor may not be required of the operator.

A further object of the present invention is to provide an interfacing method for printers, wherein a reproduced image is capable of being outputted to a sorter stage, which is one of sorter stages of a printer among a plurality of printers connected to an image information network and which corresponds to an output destination desired by an operator, such that considerable time and labor may not be required of the operator.

A still further object of the present invention is to provide an interface unit for carrying out the interfacing method for printers.

Another object of the present invention is to provide a client apparatus, which is provided with functions of the interface unit.

A further object of the present invention is to provide a method of monitoring a network printer wherein, in cases where a plurality of terminals connected to a medical network operate under management of different kinds of operating systems (OS's), a state concerning output of a network printer connected to the medical network is capable of being remote-monitored from the terminals, such that a special-purpose monitoring software functions may not be required with respect to each kind of the OS and the cost may be kept low.

A still further object of the present invention is to provide a device for carrying out the method of monitoring a network printer.

Another object of the present invention is to provide a method of managing a parameter, wherein an advantage of a conventional medical network system is obtained in that a parameter, which represents image processing conditions, or the like, for a medical image to be reproduced by each of image output devices, is capable of being altered in each of the image output devices, and wherein, in cases where a parameter is altered in one of the image output devices, the details of the alteration are capable of being reflected easily and perfectly in all of the other image output devices or in a specific one of the other image output devices.

In interfacing methods for network printers in accordance with the present invention, information (representing a kind of film, whether a state of operation is normal or abnormal, an output destination with respect to each of sorter stages, or the like) concerning each of connected network printers is recognized. In cases where a plurality of interface units are provided, the information concerning each of the connected network printers is transferred between the interface units. In every case where an output request is made to one interface unit, a printer capable of appropriately fulfilling the output request is selected, or the output request is transferred to a different interface unit, to which the printer capable of appropriately fulfilling the output request is connected.

Specifically, the present invention provides a first interfacing method, wherein a plurality of network printers, which are provided with different kinds of film for image reproduction, are connected by an interface unit to an image information network, the method comprising the steps of:

i) recognizing available kinds of film with respect to each of the network printers, which are connected to the interface unit, ii) selecting a network printer, which is among the plurality of the network printers and which corresponds to a kind of film coinciding with an output request, in accordance with the results of the recognition, and iii) giving an output instruction, which coincides with the output request, to the thus selected network printer.

The kinds of film are classified by the size of film, the base color of the film, and the like. The term "output request" as used herein means the output instruction for specifying the kind of film.

All of the plurality of the printers need not necessarily be provided with different kinds of film, and several printers among them may be provided with the same kind of film. In cases where there are at least two printers, which can carry out image reproduction on the kind of film coinciding with the output request, the order of priority may be determined previously, and one of the at least two printers may be selected in accordance with the order of priority. Alternatively, the printer, with which image reproduction is to be carried out, may be selected by combining the first interfacing method in accordance with the present invention with a third interfacing method in accordance with the present invention, which will be described later, and/or a fifth interfacing method in accordance with the present invention, which will be described later.

In the first interfacing method in accordance with the present invention, in cases where there is no network printer, which corresponds to the kind of film coinciding with the output request, a network printer, which corresponds to the kind of film closest to the kind of film coinciding with the output request, may be selected as the network printer, which corresponds to the kind of film coinciding with the output request, and an output instruction, which specifies the closest kind of film, may be given as the output instruction, which coincides with the output request, to the thus selected network printer.

In such cases, when necessary, an instruction for carrying out image size enlargement or reduction processing may also be given.

The present invention also provides a second interfacing method, wherein at least one network printer among a plurality of network printers, which are provided with different kinds of film for image reproduction, is connected by each of at least two interface units to an image information network, the method comprising the steps of, in each interface unit:

i) recognizing available kinds of film with respect to each of the at least one network printer, which is connected to the interface unit, ii) sending information, which represents the results of the recognition, to the other interface unit, iii) selecting a network printer, which is among the plurality of the network printers and which corresponds to a kind of film coinciding with an output request, in accordance with the results of the recognition and the results of recognition received from the other interface unit, or transferring the output request to the other interface unit, which is connected to the network printer to be selected, and iv) giving an output instruction, which coincides with the output request, to the thus selected network printer.

Specifically, in cases where the printer, which coincides with the output request, is connected directly to the interface unit, which received the output request, the interface unit selects the printer, which coincides with the output request, from among the printers connected to the interface unit. In cases where there is no printer, which coincides with the output request, among the printers connected directly to the interface unit, the output request is transferred to the other interface unit, which is connected to the printer that coincides with the output request.

Each time the output request is received, the information concerning each printer may be obtained of the other interface unit. Alternatively, each interface unit may be provided with a storage means, or the like. The information concerning each printer, which is received from the other interface unit, may be stored previously in the storage means. When the interface unit receives the output request, reference may be made to the information having been stored in the storage means, and the kinds of film available with each printer may thereby be recognized.

In the second interfacing method in accordance with the present invention, in cases where there is no network printer, which corresponds to the kind of film coinciding with the output request, a network printer, which corresponds to the kind of film closest to the kind of film coinciding with the output request, may be selected as the network printer, which corresponds to the kind of film coinciding with the output request, or the output request may be transferred to the other interface unit, which is connected to the network printer to be selected, and an output instruction, which specifies the closest kind of film, may be given as the output instruction, which coincides with the output request, to the thus selected network printer.

In such cases, when necessary, an instruction for carrying out image size enlargement or reduction processing may also be given.

The present invention further provides a third interfacing method, wherein a plurality of network printers are connected by an interface unit to an image information network, the method comprising the steps of:
i) recognizing whether a state of operation of each of the network printers, which are connected to the interface unit, is normal or abnormal (malfunctioning),
ii) selecting a network printer, which is among the plurality of the network printers and which is in the normal operation state, in accordance with the results of the recognition, and
iii) giving an output instruction to the thus selected network printer.

The present invention still further provides a fourth interfacing method, wherein at least one network printer among a plurality of network printers is connected by each of at least two interface units to an image information network, the method comprising the steps of, in each interface unit:
i) recognizing whether a state of operation of each of the at least one network printer, which is connected to the interface unit, is normal or abnormal,
ii) sending information, which represents the results of the recognition, to the other interface unit,
iii) selecting a network printer, which is among the plurality of the network printers and which is in the normal operation state, in accordance with the results of the recognition and the results of recognition received from the other interface unit, or transferring an output request to the other interface unit, which is connected to the network printer to be selected, and
iv) giving an output instruction to the thus selected network printer.

The present invention also provides a fifth interfacing method, wherein a plurality of network printers, each of which is provided with at least one sorter stage corresponding to an output destination, are connected by an interface unit to an image information network, the method comprising the steps of:
i) recognizing an output destination corresponding to each sorter stage of each of the network printers, which are connected to the interface unit,
ii) selecting a network printer, which is among the plurality of the network printers and which has a sorter stage corresponding to a specific output destination, in accordance with the results of the recognition, and
iii) giving an output instruction, which coincides with the specific output destination, to the thus selected network printer.

The term "output destination" as used herein means the destination to which the film outputted by the printer is to be sorted. For example, the output destinations may be classified by department into destinations for surgical diagnosis, internal diagnosis, dental diagnosis, and the like. Also, the output destinations may be classified by the kind of the object, the image of which was recorded.

The present invention further provides a sixth interfacing method, wherein at least one network printer among a plurality of network printers, each of which is provided with at least one sorter stage corresponding to an output destination, is connected by each of at least two interface units to an image information network, the method comprising the steps of, in each interface unit:
i) recognizing an output destination corresponding to each sorter stage of each of the at least one network printer, which is connected to the interface unit,
ii) sending information, which represents the results of the recognition, to the other interface unit,
iii) selecting a network printer, which is among the plurality of the network printers and which has a sorter stage corresponding to a specific output destination, in accordance with the results of the recognition and the results of recognition received from the other interface unit, or transferring an output request to the other interface unit, which is connected to the network printer to be selected, and
iv) giving an output instruction, which coincides with the specific output destination, to the thus selected network printer.

The first to sixth interfacing methods in accordance with the present invention should preferably be modified such that, in cases where each of the network printers connected to the interface unit is designed to send a monitor signal, which represents a state concerning output, in accordance with a special-purpose protocol, and each of a plurality of terminals, which constitute the image information network, is provided with general-purpose displaying software functions and operates under management with one of plural kinds of operating systems having different forms, the monitor signal having been sent in accordance with the special-purpose protocol may be converted into a signal according to a protocol, which is adapted to displaying with the displaying software functions.

The term "state concerning output" as used herein means, for example, a state concerning whether expendable supplies, such as film, paper, and toner, of the network printer have or have not run out, and a state of proceeding of output.

Also, the special-purpose protocol should preferably be a Simple Network Management Protocol (SNMP). The SNMP is one of constituent elements of a Transmission Control Protocol/Internet Protocol (TCP/IP) and has the advantages in that it is a simple protocol set and exhibits quick response.

As the displaying software functions, a World Wide Web (WWW) browser should preferably be employed. The WWW browser is the most popular displaying software functions and has a high flexibility regardless of the OS's. In cases where the WWW browser is employed as the displaying software functions, the protocol adapted to displaying may be a HyperText Transfer Protocol (or Hypertext Transport Protocol) (HTTP).

The present invention still further provides a first interface unit for carrying out the first interfacing method for network printers in accordance with the present invention. Specifically, the present invention still further provides a first interface unit for connecting a plurality of network printers, which are provided with different kinds of film for image reproduction, to an image information network, the interface unit comprising:

i) a film kind recognizing means for recognizing available kinds of film with respect to each of the network printers, which are connected to the interface unit, and ii) a printer selecting means for selecting a network printer, which is among the plurality of the network printers and which corresponds to a kind of film coinciding with an output request, in accordance with the results of the recognition having been carried out by the film kind recognizing means, wherein an output instruction, which coincides with the output request, is given to the network printer having been selected by the printer selecting means.

In the first interface unit in accordance with the present invention, in cases where there is no network printer, which corresponds to the kind of film coinciding with the output request, the printer selecting means may select a network printer, which corresponds to the kind of film closest to the kind of film coinciding with the output request, as the network printer, which corresponds to the kind of film coinciding with the output request, and an output instruction, which specifies the closest kind of film, may be given as the output instruction, which coincides with the output request, to the network printer having been selected by the printer selecting means.

The present invention also provides a second interface unit for carrying out the second interfacing method for network printers in accordance with the present invention. Specifically, the present invention also provides a second interface unit, comprising a group of at least two interface units, each of the at least two interface units connecting at least one network printer among a plurality of network printers, which are provided with different kinds of film for image reproduction, to an image information network, each interface unit comprising:

i) a film kind recognizing means for recognizing available kinds of film with respect to each of the at least one network printer, which is connected to the interface unit, and sending information, which represents the results of the recognition, to the other interface unit, and ii) a printer selecting means for selecting a network printer, which is among the plurality of the network printers and which corresponds to a kind of film coinciding with an output request, in accordance with the results of the recognition having been carried out by the film kind recognizing means and the results of recognition received from the other interface unit, or transferring the output request to the other interface unit, which is connected to the network printer to be selected, wherein an output instruction, which coincides with the output request, is given to the network printer having been selected by the printer selecting means.

In the second interface unit in accordance with the present invention, in cases where there is no network printer, which corresponds to the kind of film coinciding with the output request, the printer selecting means may select a network printer, which corresponds to the kind of film closest to the kind of film coinciding with the output request, as the network printer, which corresponds to the kind of film coinciding with the output request, or may transfer the output request to the other interface unit, which is connected to the network printer to be selected, and an output instruction, which specifies the closest kind of film, may be given as the output instruction, which coincides with the output request, to the network printer having been selected by the printer selecting means.

The present invention further provides a third interface unit for carrying out the third interfacing method for network printers in accordance with the present invention. Specifically, the present invention further provides a third interface unit for connecting a plurality of network printers to an image information network, the interface unit comprising:

i) an operation state recognizing means for recognizing whether a state of operation of each of the network printers, which are connected to the interface unit, is normal or abnormal, and ii) a printer selecting means for selecting a network printer, which is among the plurality of the network printers and which is in the normal operation state, in accordance with the results of the recognition having been carried out by the operation state recognizing means, wherein an output instruction is given to the network printer having been selected by the printer selecting means.

The present invention still further provides a fourth interface unit for carrying out the fourth interfacing method for network printers in accordance with the present invention. Specifically, the present invention still further provides a fourth interface unit, comprising a group of at least two interface units, each of the at least two interface units connecting at least one network printer among a plurality of network printers to an image information network, each interface unit comprising:

i) an operation state recognizing means for recognizing whether a state of operation of each of the at least one network printer, which is connected to the interface unit, is normal or abnormal, and sending information, which represents the results of the recognition, to the other interface unit, and ii) a printer selecting means for selecting a network printer, which is among the plurality of the network printers and which is in the normal operation state, in accordance with the results of the recognition having been carried out by the operation state recognizing means and the results of recognition received from the other interface unit, or transferring an output request to the other interface unit, which is connected to the network printer to be selected, wherein an output instruction is given to the network printer having been selected by the printer selecting means.

The present invention also provides a fifth interface unit for carrying out the fifth interfacing method for network printers in accordance with the present invention. Specifically, the present invention also provides a fifth interface unit for connecting a plurality of network printers, each of which is provided with at least one sorter stage corresponding to an output destination, to an image information network, the interface unit comprising:

i) an output destination recognizing means for recognizing an output destination corresponding to each sorter stage of each of the network printers, which are connected to the interface unit, and ii) a printer selecting means for selecting a network printer, which is among the plurality of the network printers and which has a sorter stage corresponding to a specific output destination, in accordance with the results of the recognition having been carried out by the output destination recognizing means, wherein an output instruction, which coincides with the specific output destination, is given to the network printer having been selected by the printer selecting means.

The present invention further provides a sixth interface unit for carrying out the sixth interfacing method for network printers in accordance with the present invention. Specifically, the present invention further provides a sixth interface unit, comprising a group of at least two interface units, each of the at least two interface units connecting at least one network printer among a plurality of network printers, each of which is provided with at least one sorter stage corresponding to an output destination, to an image information network, each interface unit comprising:

i) an output destination recognizing means for recognizing an output destination corresponding to each sorter stage of each of the at least one network printer, which is connected to the interface unit, and sending information, which represents the results of the recognition, to the other interface unit, and ii) a printer selecting means for selecting a network printer, which is among the plurality of the network printers and which has a sorter stage corresponding to a specific output destination, in accordance with the results of the recognition having been carried out by the output destination recognizing means and the results of recognition received from the other interface unit, or transferring an output request to the other interface unit, which is connected to the network printer to be selected, wherein an output instruction, which coincides with the specific output destination, is given to the network printer having been selected by the printer selecting means.

The first to sixth interface units in accordance with the present invention should preferably be modified such that, in cases where each of the network printers connected to the interface unit is designed to send a monitor signal, which represents a state concerning output, in accordance with a special-purpose protocol, and each of a plurality of terminals, which constitute the image information network, is provided with general-purpose displaying software functions and operates under management with one of plural kinds of operating systems having different forms, the interface unit may further comprise a protocol converting means for converting the monitor signal, which has been sent in accordance with the special-purpose protocol, into a signal according to a protocol, which is adapted to displaying with the displaying software functions.

The functions of each of the first to sixth interface units in accordance with the present invention may be provided on the side of a client apparatus. In such cases, the interfacing of the client apparatus and printers may be carried out through a network or through other means, such as parallel connection.

A method and device for monitoring a network printer in accordance with the present invention are characterized by converting a monitor signal, which is fed out by a network printer in accordance with a special-purpose protocol, in a network into a signal according to a protocol, which is adapted to displaying with general-purpose displaying software functions, such that a state concerning output of the printer can be monitored with each of a plurality of terminals, which are provided with general-purpose displaying software functions and operate under management with different kinds of operating systems.

Specifically, the present invention still further provides a method of monitoring a network printer in a medical network, wherein a network printer designed to send a monitor signal, which represents a state concerning output, in accordance with a special-purpose protocol may be connected to a plurality of terminals, each of which is provided with general-purpose displaying software functions and operates under management with one of plural kinds of operating systems having different forms, the method comprising:

converting the monitor signal, which has been sent in accordance with the special-purpose protocol, into a signal according to a protocol, which is adapted to displaying with the displaying software functions.

The present invention also provides a device for carrying out the method of monitoring a network printer in accordance with the present invention. Specifically, the present invention also provides a device for monitoring a network printer for use in a medical network, wherein a network printer designed to send a monitor signal, which represents a state concerning output, in accordance with a special-purpose protocol may be connected to a plurality of terminals, each of which is provided with general-purpose displaying software functions and operates under management with one of plural kinds of operating systems having different forms, the device comprising:

a protocol converting means for converting the monitor signal, which has been sent in accordance with the special-purpose protocol, into a signal according to a protocol, which is adapted to displaying with the displaying software functions.

The present invention further provides a method of managing a parameter in a system constituted of a plurality of image output devices, which reproduce medical images and are connected to a network, the parameter representing image processing conditions, or the like, for a medical image to be reproduced by each of the image output devices, the method comprising the steps of:

i) transferring information, which represents a parameter having been altered in one of the image output devices, into at least one image output device among the other image output devices, and ii) causing the at least one image output device among the other image output devices to carry out image processing by selectively using the parameter, which has been transferred, or a parameter, which has been set previously in the at least one image output device among the other image output devices.

The information, which represents a parameter having been altered in one of the image output devices, may be transferred into image output devices, which are among the other image output devices and are specified under predetermined conditions, such as an individual device, the kind of device, a diagnosis department, a device for reproducing images of the same patient, or a device for reproducing images for the same examination.

The image output device, to which the information representing the parameter having been altered is to be transferred, may be specified in the manner described below. Specifically, the parameter may correspond to index information, which represents an image recording menu of the medical image to be reproduced by each of the image output devices, information specifying an image output device, which has the same index information as the index information of each of the image output devices, may be entered previously, at least one image output device, which is among the other image output devices and has the index information corresponding to the parameter having been altered, may be specified by making reference to the entered information, and the information, which represents the parameter having been altered, may be transferred into the at least one image output device, which is among the other image output devices and has thus been specified.

The term "image recording menu" as used herein means the item representing the kind of the medical image having been recorded. For example, the image recording menu is the item altered in accordance with the conditions for image processing, such as the image recording apparatus with which the image was recorded, the date of the image recording, the diagnosis department, the name of patient, the kind of examination (mass medical examinations, a close examination, or the like), and the portion of the object the image of which was recorded (the chest, the abdomen, or the like). The term "index information" as used herein means the code number, or the like, which are set to correspond to each image recording menu, such that various image recording menus can be discriminated from one another.

The present invention still further provides a system for carrying out the method of managing a parameter in accordance with the present invention. Specifically, the present invention still further provides a system for managing a parameter, wherein a plurality of image output devices which reproduce medical images, are connected to a network, and a parameter, which represents image processing conditions, or the like, for a medical image to be reproduced by each of the image output devices, is managed, the system comprising, provided in each image output device:

i) a parameter altering means for altering a parameter, ii) a transfer means for transferring information, which represents the parameter having been altered, into at least one image output device among the other image output devices, iii) a receiving means for receiving the transferred information, which represents the parameter having been altered, and iv) an image processing means for carrying out image processing by selectively using the parameter, which has been received, or a parameter, which has been set previously in the each image output device.

In the system for managing a parameter in accordance with the present invention, the transfer means may transfer the information, which represents the parameter having been altered, into at least one image output device among the other image output devices, which has been specified under predetermined conditions.

The system for managing a parameter in accordance with the present invention, wherein the transfer means transfers the information, which represents the parameter having been altered, into at least one image output device, which has been specified under predetermined conditions, may be modified in the manner described below. Specifically, the parameter may correspond to index information, which represents an image recording menu of the medical image to be reproduced by each of the image output devices, each of the image output devices may be provided with an entry means for previously entering information specifying an image output device, which has the same index information as the index information of each of the image output devices, and the transfer means may specify at least one image output device, which is among the other image output devices and has the index information corresponding to the parameter having been altered, by making reference to the information having been entered by the entry means, and may transfer the information, which represents the parameter having been altered, into the at least one image output device, which is among the other image output devices and has thus been specified.

The parameter may be stored in one of various ways, in which the parameter can be used arbitrarily in carrying out image processing, and the like, in each of the image output devices. Particularly, from the view point of facilitating the parameter management, the parameter should preferably be stored as a data base in a storage device, such as a hard disk, provided in each of the image output devices.

In the system for managing a parameter in accordance with the present invention, the image output devices may be embodied in one of various ways, such that a visible image can be reproduced. For example, the image output devices may be soft copy devices, such as CRT display devices, or hard copy devices, such as LP's.

With the interfacing methods and the interface units for network printers in accordance with the present invention, the information (representing a kind of film, whether a state of operation is normal or abnormal, an output destination with respect to each of sorter stages, or the like) concerning each of the connected network printers is recognized by the interface unit (or each of the interface units in cases where a plurality of interface units are provided). Therefore, the plurality of the interface units, which are connected to the network, can be processed virtually as a single printer. In cases where the output request is made to the interface unit, a printer, which can appropriately cope with the output request, is selected, or the output request is transferred to the other interface unit, which is connected to such a printer. Therefore, it is unnecessary for the operator to consider which printer can output which kind of film. The operator may merely make the output request to one of the printers, and can thereby obtain the desired film and the desired image from a printer, which can fulfill the output request.

Also, it is unnecessary for the operator to consider which printer is currently malfunctioning. The operator may merely make the output request to one of the printers, and can thereby obtain the desired film and the desired image from a printer, which is currently operable normally.

Further, it is unnecessary for the operator to consider which printer has the sorter stage for the desired destination.

The operator may merely send the output instruction to one of the printers, and can thereby obtain the desired film and the desired image from a printer, which has the sorter stage appropriate for the output instruction.

With the client apparatus in accordance with the present invention, the same effects as those described above can be obtained.

With the method and device for monitoring a network printer in accordance with the present invention, the monitor signal, which represents the state concerning output of the network printer and has been fed out in accordance with the special-purpose protocol by the network printer connected to the medical network, is converted into the signal according to a protocol, which is adapted to displaying with general-purpose displaying software functions. The converted signal is sent to the terminals. Therefore, even if the terminals, which may be connected to the medical network, are a plurality of terminals, which can operate only under management with different kinds of operating systems, the monitor signal can be remote-monitored at every terminal with its general-purpose displaying software functions.

Also, the displaying software functions, which each terminal has, are the general-purpose displaying software functions regardless of the kind of the OS, it is unnecessary for the special-purpose software functions for monitoring the state of output to be provided with respect to each of various kinds of OS s. Therefore, the monitoring of the network printer can be achieved at a low cost.

With the method and system for managing a parameter in accordance with the present invention, in cases where the parameter is altered in one of the image output devices, the details of the alteration are transferred to the other image output devices. The other image output devices, which have received the details of the alteration, carry out the image processing by selectively using the received parameter or the parameter, which has previously set in each of the other image output devices. Therefore, when necessary, the same parameter as the parameter having been altered in one image output device can be utilized reliably in the other image output devices. Accordingly, considerable time and labor are not required to alter the parameter in the other image output devices. Also, in cases where the received parameter is always selected, the alteration can be carried out perfectly.

Further, in cases where the transfer of the details of the alteration is carried out by specifying the image output device, which should receive the details of the alteration, the image output device, in which the parameter should be updated, can be specified from the image output device, from which the details of the alteration are transferred. The image output device, which should receive the details of the alteration, can be specified by the utilization of the index information, which represents the kind of the recorded image. Therefore, the transfer can be carried out by specifying an image output device and, for example, the kind of the image, such as the image of a specific patient and the image for the same purposes of examination.

DESCRIPTION OF THE PREFERRED EMBODIMENTS

The present invention will hereinbelow be described in further detail with reference to the accompanying drawings.

Embodiments of the interface unit for network printers in accordance with the present invention will firstly be described hereinbelow.

Figure 1:
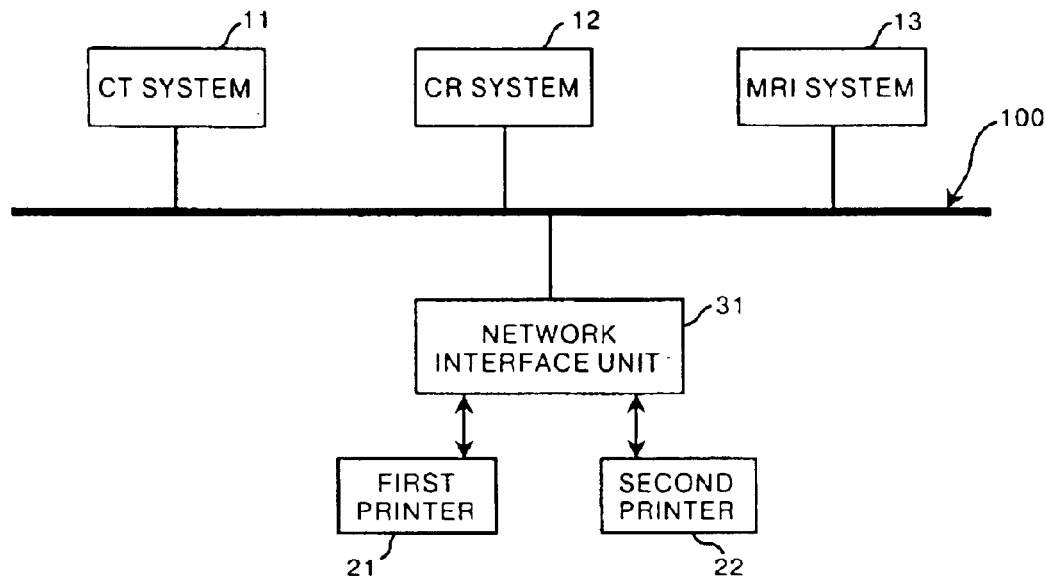
FIG. 1 is a block diagram showing a network, in which an embodiment of the first, third, or fifth interface unit in accordance with the present invention is employed.

FIG. 1 shows a network 100, in which an embodiment of the first interface unit in accordance with the present invention is employed.

With reference to FIG. 1, the network 100 is a medical image network for processing medical images. The network 100 is connected to a CT system 11, a CR system 12, and an MRI system 13, which are image information input modalities. The network 100 is also connected to two network printers, i.e. a first printer 21 and a second printer 22, which serve as image output devices.

The first printer 21 and the second printer 22 reproduce images on different kinds of film. The first printer 21 outputs film in which the base color is clear. The second printer 22 outputs film in which the base color is blue. The first printer 21 and the second printer 22 are connected via a network interface unit 31 to the network.

Figure 2:
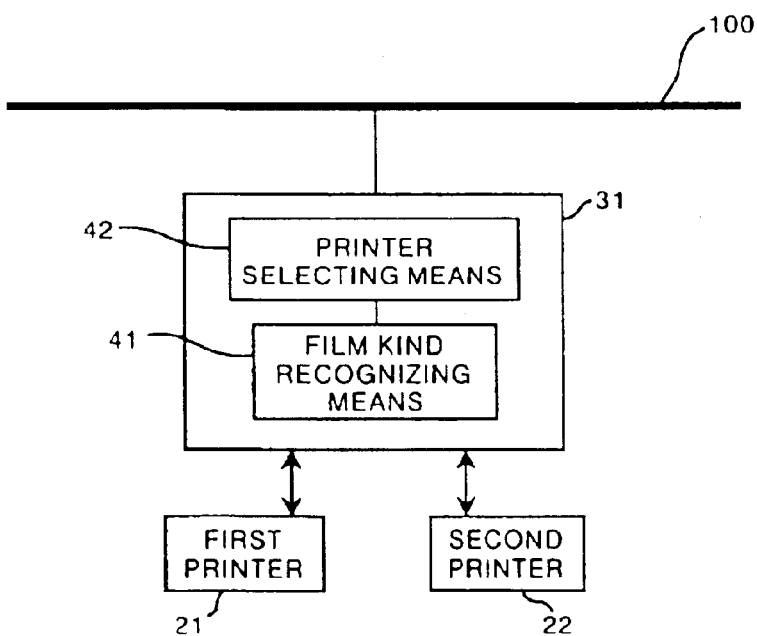
FIG. 2 is a block diagram showing details of the embodiment of the first interface unit in accordance with the present invention.

As illustrated in detail in FIG. 2, the network interface unit 31 comprises a film kind recognizing means 41 and a printer selecting means 42. The film kind recognizing means 41 recognizes available kinds of film, which can be outputted by each of the first printer 21 and the second printer 22. In accordance with the results of the recognition having been carried out by the film kind recognizing means 41, the printer selecting means 42 selects the first printer 21 or the second printer 22, which corresponds to a kind of film (a base color) coinciding with an output request. The network interface unit 31 gives an output instruction, which coincides with the output request, to the first printer 21 or the second printer 22, which is selected by the printer selecting means 42.

For example, an output request for reproducing image information, which has been obtained with the CR system 12, on film having a blue base color, may be made from a terminal (not shown), which is connected to the network 100. In such cases, the output request is inputted via the network 100 into the network interface unit 31.

In the network interface unit 31, the film kind recognizing means 41 recognizes previously that the first printer 21 connected to the network interface unit 31 can output film having a clear base color, and that the second printer 22 can output film having a blue base color. In accordance with the results of the recognition having been carried out by the film kind recognizing means 41, the printer selecting means 42 selects the second printer 22, which coincides with the output request (for reproducing image information, which has been obtained with the CR system 12, on film having a blue base color) having been received from the network 100. An instruction for image reproduction is sent to the second printer 22.

As a result, the image information having been obtained with the CR system 12 is reproduced by the second printer 22 as a visible image on film having a blue base color.

As described above, with this embodiment of the network interface unit 31, it is unnecessary for the operator, who enters the output request to the terminal, to consider which printer can output which kind of film, and the operator can enter the output request in a way such that he may virtually enter the output request to a single printer. Therefore, burden to the operator can be relieved.

In the embodiment of the interface unit described above, two printers are connected to the network interface unit 31. However, the first interface unit in accordance with the present invention is not limited to the embodiment described above, and at least three printers may be connected to the interface unit. As the number of the connected printers becomes large, the effects of relieving the burden to the operator become large.

Also, in the embodiment of the interface unit described above, the base color is exemplified as the kind of film. As the kind of film, the film size (a 14"×17" size, a 14"×14" size, a 10"×14" size, an 8"×10" size, or the like) may also be employed. For example, the first printer 21 can selectively output film having a 14"×17" size or a 14"×14" size. The second printer 22 can selectively output film having a 10"×14" size or an 8"×10" size. In such cases, the film kind recognizing means 41 of the network interface unit 31 recognizes the information representing the film size. In accordance with the results of recognition having been carried out by the film kind recognizing means 41, the printer selecting means 42 selects, for example, the first printer 21, which coincides with the output request (for reproducing image information on film having, for example, a 14"×17" size) having been received from the network 100. An instruction for image reproduction is sent to the first printer 21. In this manner, it is unnecessary for the operator to consider which printer can output the film of the desired kind, and the operator can obtain the image having been reproduced on the film having a 14"×17" size from the first printer 21.

In the embodiment of the interface unit described above, in cases where there is no network printer, which corresponds to the kind of film coinciding with the output request, the printer selecting means may select a network printer, which corresponds to the kind of film closest to the kind of film coinciding with the output request, as the network printer, which corresponds to the kind of film coinciding with the output request. Also, an output instruction, which specifies the closest kind of film, may be given as the output instruction, which coincides with the output request, to the network printer having been selected by the printer selecting means. In such cases, when necessary, an instruction for carrying out image size enlargement or reduction processing may also be given.

Figure 3:
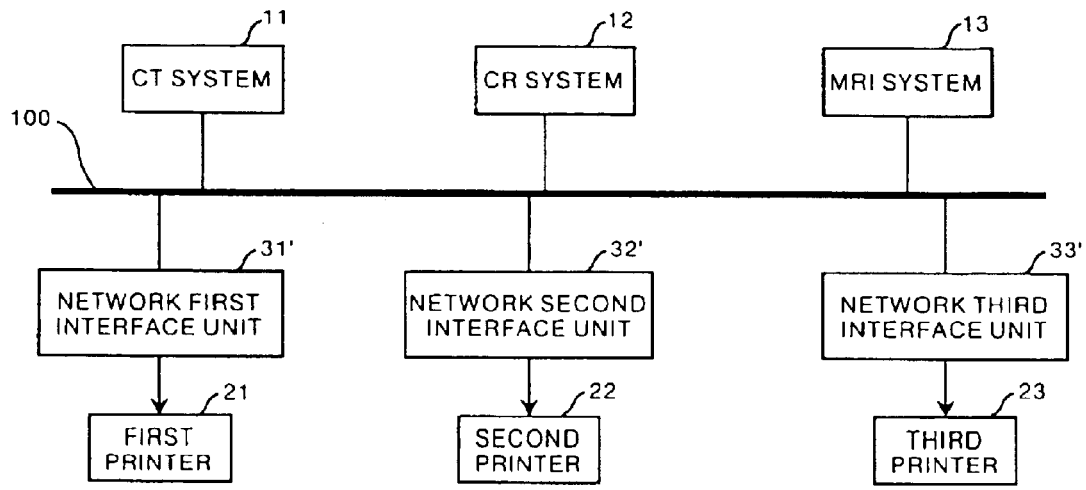
FIG. 3 is a block diagram showing an example of a network, in which an embodiment of the second, fourth, or sixth interface unit in accordance with the present invention is employed.
Figure 4:
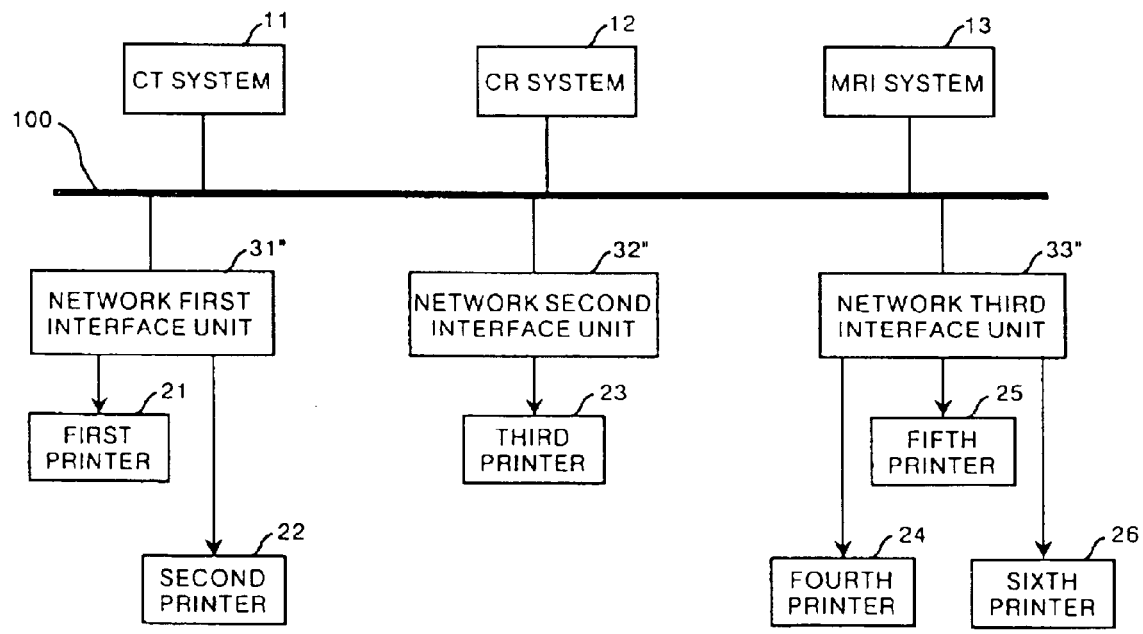
FIG. 4 is a block diagram showing a different example of a network, in which an embodiment of the second, fourth, or sixth interface unit in accordance with the present invention is employed.

In the embodiment of FIG. 1, only one interface unit is provided. However, the number of the interface units is not limited to one. For example, as illustrated in FIG. 3, one interface unit may be provided for each printer, and a plurality of interface units may thus be provided. Alternatively, as illustrated in FIG. 4, one printer or at least two printers may be connected to each interface unit, and a plurality of interface units may thus be provided. Such constitutions having plurality of interface units constitute embodiments of the second interface unit in accordance with the present invention.

Specifically, the network 100 shown in FIG. 3 is connected to the CT system 11, the CR system 12, and the MRI system 13, which are image information input modalities. The network 100 is also connected to three network printers, i.e. the first printer 21, the second printer 22, and a third printer 23, which serve as image output devices.

The first printer 21, the second printer 22, and the third printer 23 reproduce images on different kinds of film. The first printer 21 outputs film having a 14"×17" size. The second printer 22 outputs film having a 14"×14" size. The third printer 23 outputs film having a 14"×14" size or an 8"×10" size. The first printer 21 is connected via a network first interface unit 31' to the network. The second printer 22 is connected via a network second interface unit 32' to the network. The third printer 23 is connected via a network third interface unit 33' to the network.

Figure 5:
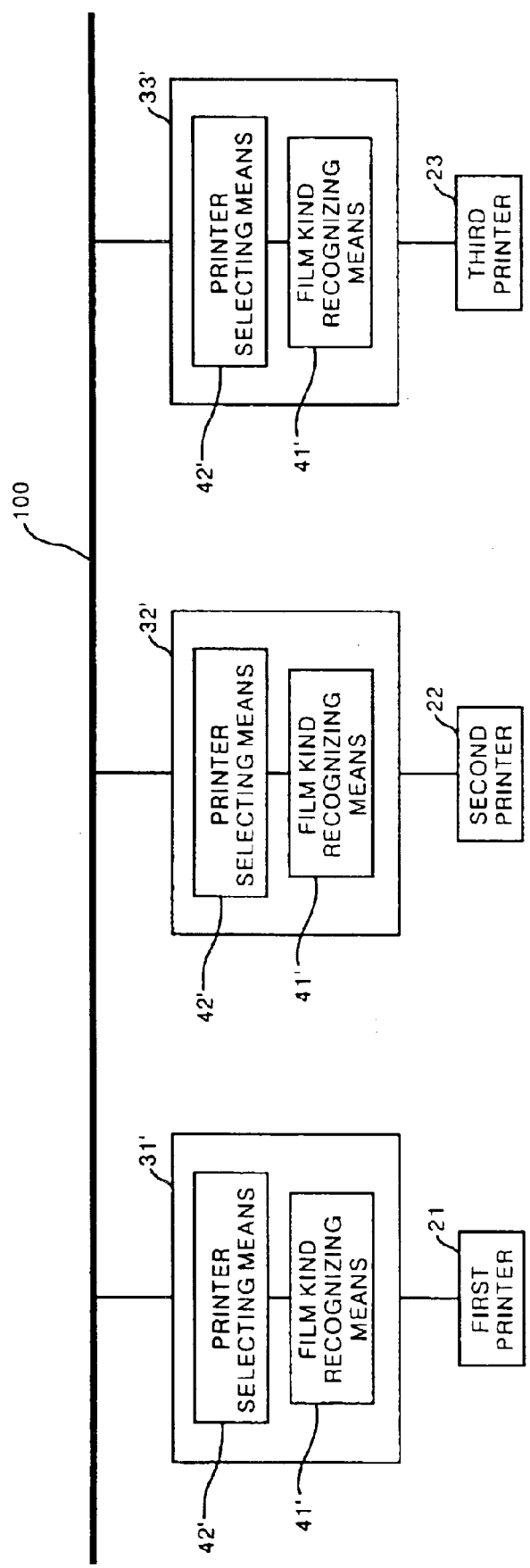
FIG. 5 is a block diagram showing details of the embodiment of the second interface unit in accordance with the present invention.

As illustrated in detail in FIG. 5, each of the network first interface unit 31', the network second interface unit 32', and the network third interface unit 33', comprises a film kind recognizing means 41' and a printer selecting means 42'. Each film kind recognizing means 41' recognizes available kinds of film (the film size), which can be outputted by the corresponding one of the first printer 21, the second printer 22, and the third printer 23, which are respectively connected to the network first interface unit 31', the network second interface unit 32', and the network third interface unit 33'. Also, the film kind recognizing means 41' sends information, which represents the available kinds of film, to the other interface units. In accordance with the results of the recognition having been carried out by the film kind recognizing means 41' and the film information, which concerns the printers connected to the other interface units and which has been received from the film kind recognizing means 41', 41' of the other interface units, the printer selecting means 42' selects a printer, which corresponds to a kind of film (a film size) coinciding with an output request. Alternatively, the printer selecting means 42' transfers the output request to one of the other interface units, which is connected to the printer to be selected. An output instruction, which coincides with the output request, is given to the printer, which has been selected by the printer selecting means 42', or to the printer having been selected by the printer selecting means of the interface unit, to which the output request has been transferred.

For example, an output request for reproducing image information, which has been obtained with the CR system 12, on film having a 14"×14" size, may be made from a terminal (not shown), which is connected to the network 100. In such cases, the output request is inputted via the network 100 into, for example, the network first interface unit 31'. Alternatively, the output request may be inputted into the network second interface unit 32' or the network third interface unit 33'.

In each of the network first interface unit 31', the network second interface unit 32', and the network third interface unit

33', the film kind recognizing means 41' recognizes previously the film size, which can be outputted by the corresponding printer 21, 22, or 23 directly connected to the film kind recognizing means 41'. Also, the film kind recognizing means 41' sends the size information to the other interface units.

In this manner, each of the network first interface unit 31', the network second interface unit 32', and the network third interface unit 33' can recognize the available film sizes, which can be outputted by all of the printers 21, 22, and 23.

Thereafter, in accordance with the results of the recognition having been carried out by the film kind recognizing means 41', the printer selecting means 42' of the network first interface unit 31' finds a printer, which coincides with the output request (for reproducing image information, which has been obtained with the CR system 12, on film having a 14"×14" size) having been received from the network 100. The printer selecting means 42' thus recognizes that the coinciding printer is the second printer 22. In this case, the interface unit, to which the second printer 22 is connected, is the network second interface unit 32'. Therefore, the printer selecting means 42' of the network first interface unit 31' transfers the received output request via the network 100 into the network second interface unit 32'.

In the network second interface unit 32', which has received the output request, the printer selecting means 42' selects the second printer 22 coinciding with the output request and gives an instruction for image reproduction to the second printer 22.

As a result, the image information having been obtained with the CR system 12 is reproduced by the second printer 22 as a visible image on film having a 14"×14" size.

As described above, this embodiment comprising the interface units 31', 32', and 33', it is unnecessary for the operator, who enters the output request to the terminal, to consider which printer can output which kind of film, and the operator can enter the output request in a way such that he may virtually enter the output request to a single printer. Therefore, burden to the operator can be relieved.

FIG. 4 shows an embodiment, wherein each interface unit is connected to one printer or at least two printers, and a plurality of interface units are thus provided. Specifically, the first printer 21 and the second printer 22 are connected to a first interface unit 31", and only the third printer 23 is connected to a second interface unit 32". Also, a fourth printer 24, a fifth printer 25, and a sixth printer 26 are connected to a third interface unit 33".

The first printer 21, the second printer 22, and the third printer 23 reproduce images on different kinds of film having different combinations of the film size and the film base color.

As in the interface units 31', 32', and 33' illustrated in FIG. 5, each of the interface units 31", 32", and 33" comprises the film kind recognizing means 41' and the printer selecting means 42'. Each film kind recognizing means 41' recognizes available kinds of film (the combination of the film size and the film base color), which can be outputted by the corresponding printer. Also, the film kind recognizing means 41' sends information, which represents the available kinds of film, to the other interface units. In accordance with the results of the recognition having been carried out by the film kind recognizing means 41' and the film information, which concerns the printers connected to the other interface units and which has been received from the film kind recognizing means 41', 41' of the other interface units, the printer selecting means 42' selects a printer, which corresponds to a kind of film coinciding with an output request. Alternatively, the printer selecting means 42' transfers the output request to one of the other interface units, which is connected to the printer to be selected. An output instruction, which coincides with the output request, is given to the printer, which has been selected by the printer selecting means 42', or to the printer having been selected by the printer selecting means of the interface unit, to which the output request has been transferred.

The operations and the effects of the interface units 31", 32", and 33" are the same as those of the interface units 31', 32', and 33' shown in FIG. 3.

In the embodiments of FIGS. 3 and 4, in cases where there is no network printer, which corresponds to the kind of film coinciding with the output request, the printer selecting means may select a network printer, which corresponds to the kind of film closest to the kind of film coinciding with the output request, as the network printer, which corresponds to the kind of film coinciding with the output request, or may transfer the output request to the other interface unit, which is connected to the network printer to be selected. Also, an output instruction, which specifies the closest kind of film, may be given as the output instruction, which coincides with the output request, to the network printer having been selected by the printer selecting means. In such cases, when necessary, an instruction for carrying out image size enlargement or reduction processing may also be given.

An embodiment of the third interface unit in accordance with the present invention will be described hereinbelow. In this embodiment, the first printer 21 and the second printer 22, which are connected to the network 100 shown in FIG. 1, may reproduce images on the sake kind of film, and the network interface unit 31 shown in FIG. 1 may have the constitution shown in FIG. 6.

Specifically, in the embodiment of the third interface unit in accordance with the present invention, the first printer 21 and the second printer 22 reproduce images on sheets of film having the same size and the same base color. In this case, it is assumed that the first printer 21 is malfunctioning, and the second printer 22 can operate normally.

Figure 6:
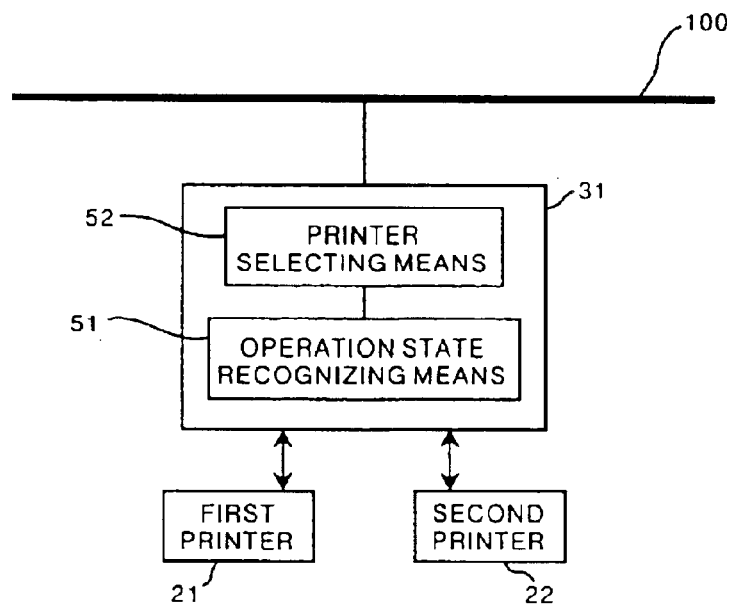
FIG. 6 is a block diagram showing details of the embodiment of the third interface unit in accordance with the present invention.

As illustrated in FIG. 6, the network interface unit 31 comprises an operation state recognizing means 51 for recognizing whether a state of operation of each of the printers 21 and 22, which are connected to the network interface unit 31, is normal or abnormal (malfunctioning). The network interface unit 31 also comprises a printer selecting means 52 for selecting the first printer 21 or the second printer 22, which is in the normal operation state, in accordance with the results of the recognition having been carried out by the operation state recognizing means 51. An output instruction coinciding with an output request is given to the printer 21 or 22, which has been selected by the printer selecting means 52.

For example, an output request for reproducing image information, which has been obtained with the CR system 12, on film may be made from a terminal (not shown), which is connected to the network 100. In such cases, the output request is inputted via the network 100 into the network interface unit 31.

In the network interface unit 31, the operation state recognizing means 51 recognizes previously a state of operation (a normally operable state or a malfunctioning state) of each of the first printer 21 and the second printer 22, which are connected to the network interface unit 31. In this embodiment, it is recognized that the first printer 21 is malfunctioning, and the second printer 22 is normally operable. In accordance with the results of the recognition having been carried out by the operation state recognizing means 51, the printer selecting means 52 selects the second printer 22, which can cope with the output request having been received from the network 100, i.e. which is normally operable. An instruction for image reproduction is sent to the second printer 22.

As a result, the image information having been obtained with the CR system 12 is reproduced by the second printer 22 as a visible image on the film.

As described above, with this embodiment of the network interface unit 31, it is unnecessary for the operator, who enters the output request to the terminal, to consider which printer is malfunctioning, and the operator can enter the output request in a way such that he may virtually enter the output request to a single printer. Therefore, burden to the operator can be relieved.

In this embodiment of the third interface unit described above, two printers are connected to the network interface unit 31. However, the third interface unit in accordance with the present invention is not limited to the embodiment described above, and at least three printers may be connected to the interface unit. As the number of the connected printers becomes large, the effects of relieving the burden to the operator become large.

Also, in the embodiment of the third interface unit described above with reference to FIG. 1, only one interface unit is provided. Alternatively, as illustrated in FIG. 3, one interface unit may be provided for each printer, and a plurality of interface units may thus be provided. As another alternative, as illustrated in FIG. 4, one printer or at least two printers may be connected to each interface unit, and a plurality of interface units may thus be provided. Such constitutions having plurality of interface units constitute embodiments of the fourth interface unit in accordance with the present invention.

In the embodiments of the fourth interface unit in accordance with the present invention, wherein a plurality of interface units are provided, the operation state recognizing means 51 shown in FIG. 6 recognizes the state of operation (the normally operable state or the malfunctioning state) of each connected printer and sends information, which represents the results of the recognition, to the other interface units. In accordance with the results of the recognition having been carried out by the operation state recognizing means 51 and the information, which represents the results of recognition and which has been received from the other interface units, the printer selecting means 52 selects a printer, which is in the normally operable state. Alternatively, the printer selecting means 52 transfers the output request to one of the other interface units, which is connected to the printer to be selected.

With the embodiment comprising the interface units 31', 32', and 33' or with the embodiment comprising the 31", 32", and 33", it is unnecessary for the operator, who enters the output request to the terminal, to consider which printer is malfunctioning, and the operator can enter the output request in a way such that he may virtually enter the output request to a single printer. Therefore, burden to the operator can be relieved.

An embodiment of the fifth interface unit in accordance with the present invention will be described hereinbelow. In this embodiment, each of the first printer 21 and the second printer 22, which are connected to the network 100 shown in FIG. 1, may have a sorter combined with each printer. Each sorter may have, for example, three sorter stages, which correspond to different output destinations.

Specifically, the sorter stages are set for destinations, to which the film is to be sorted. For example, as for the sorter of the first printer 21, a first stage may be set for the surgical department, a second stage may be set for the department of plastic surgery, and a third stage may be set for the department of cerebral surgery. As for the sorter of the second printer 22, a first stage may be set for the first internal department, a second stage may be set for the second internal department, and a third stage may be set for the dental department. Film, which has been outputted to the second stage of the sorter of the second printer 22, is sorted for the second internal department.

Figure 7:
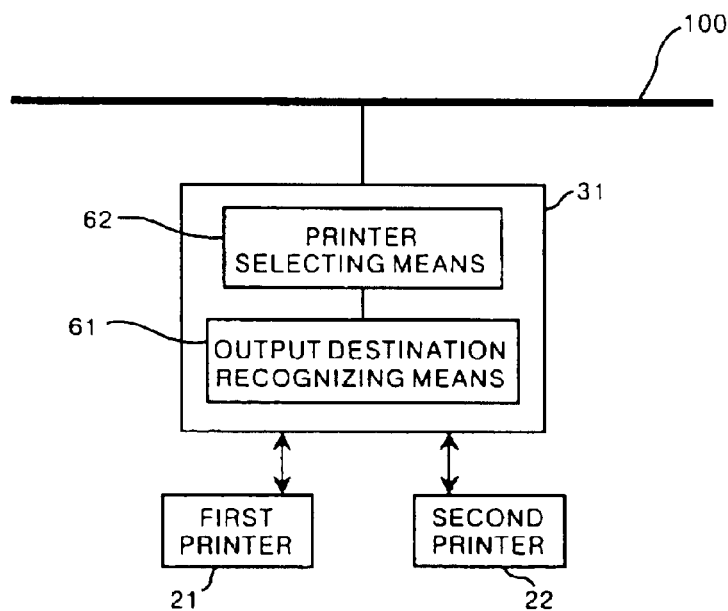
FIG. 7 is a block diagram showing details of the embodiment of the fifth interface unit in accordance with the present invention.

In this embodiment, the network interface unit 31 has the constitution shown in FIG. 7.

Specifically, as illustrated in FIG. 7, the network interface unit 31 comprises an output destination recognizing means 61 for recognizing an output destination corresponding to each sorter stage of each of the printers 21 and 22, which are connected to the interface unit. The network interface unit 31 also comprises a printer selecting means 62 for selecting the printer 21 or 22, which has a sorter stage corresponding to a specific output destination, in accordance with the results of the recognition having been carried out by the output destination recognizing means 61. An output instruction, which coincides with the output request, is given to the printer 21 or 22 having been selected by the printer selecting means 62.

For example, an output request for reproducing image information, which has been obtained with the CR system 12, on film and as an image to be sorted to the second internal department may be made from a terminal (not shown), which is connected to the network 100. In such cases, the output request is inputted via the network 100 into the network interface unit 31.

In the network interface unit 31, the output destination recognizing means 61 recognizes previously the output destination of each of the stages of the sorter of the first printer 21, which is connected to the network interface unit 31, and the output destination of each of the stages of the sorter of the second printer 22. In this embodiment, as described above, the sorter stages are set for output destinations such that, as for the sorter of the first printer 21, the first stage may be set for the surgical department, the second stage may be set for the department of plastic surgery, and the third stage may be set for the department of cerebral surgery. As for the sorter of the second printer 22, the first stage is set for the first internal department, the second stage is set for the second internal department, and the third stage is set for the dental department. The output destination recognizing means 61 recognizes the output destinations and the corresponding sorter stages of the sorters of the printers.

Thereafter, in accordance with the results of the recognition having been carried out by the output destination recognizing means 61, the printer selecting means 62 selects a printer, which has the sorter stage for the output destination corresponding to the output request (for reproducing image information, which has been obtained with the CR system 12, on film and as an image to be sorted to the second internal department) having been received from the network 100, i.e. the second printer 22. An instruction for reproducing an image and sorting it to the second stage of the sorter is sent to the second printer 22.

As a result, the image information having been obtained with the CR system 12 is reproduced by the second printer 22 as a visible image on the film and sorted and discharged to the second stage of the sorter.

As described above, with this embodiment of the network interface unit 31, it is unnecessary for the operator, who enters the output request to the terminal, to consider to which sorter stage of which printer the film must be sorted, and the operator can enter the output request in a way such that he may virtually enter the output request to a single printer. Therefore, burden to the operator can be relieved.

In this embodiment of the fifth interface unit described above, two printers are connected to the network interface unit 31. However, the fifth interface unit in accordance with the present invention is not limited to the embodiment described above, and at least three printers may be connected to the interface unit. As the number of the connected printers becomes large, the effects of relieving the burden to the operator become large.

Also, in the embodiment of the fifth interface unit described above with reference to FIG. 1, only one interface unit is provided. Alternatively, as illustrated in FIG. 3, one interface unit may be provided for each printer, and a plurality of interface units may thus be provided. As another alternative, as illustrated in FIG. 4, one printer or at least two printers may be connected to each interface unit, and a plurality of interface units may thus be provided. Such constitutions having plurality of interface units constitute embodiments of the sixth interface unit in accordance with the present invention.

In the embodiments of the sixth interface unit in accordance with the present invention, wherein a plurality of interface units are provided, the output destination recognizing means 61 shown in FIG. 7 recognizes the output destination of each sorter stage of each connected printer and sends information, which represents the results of the recognition, to the other interface units. In accordance with the results of the recognition having been carried out by the output destination recognizing means 61 and the information, which represents the results of recognition and which has been received from the other interface units, the printer selecting means 62 selects a printer, which has the sorter stage for the desired output destination. Alternatively, the printer selecting means 62 transfers the output request to one of the other interface units, which is connected to the printer to be selected.

With the embodiment comprising the interface units 31', 32', and 33' or with the embodiment comprising the 31", 32", and 33", it is unnecessary for the operator, who enters the output request to the terminal, to consider to which sorter stage of which printer the film must be sorted, and the operator can enter the output request in a way such that he may virtually enter the output request to a single printer. Therefore, burden to the operator can be relieved.

The classification of the output destinations corresponding to the sorter stages is not limited to the classification by diagnosis department. For example, the output destinations may be classified by patient.

Each of the aforesaid embodiments of the first to sixth interface units in accordance with the present invention may also be provided with a protocol converting means in a device for monitoring a network printer, which will be described later.

Also, the functions of each of the first to sixth interface units in accordance with the present invention may be provided on the side of a client apparatus. In such cases, the interfacing of the client apparatus and printers may be carried out through a network or through other means, such as parallel connection.

An embodiment of the device for monitoring a network printer in a medical network in accordance with the present invention will be described hereinbelow.

Figure 8:
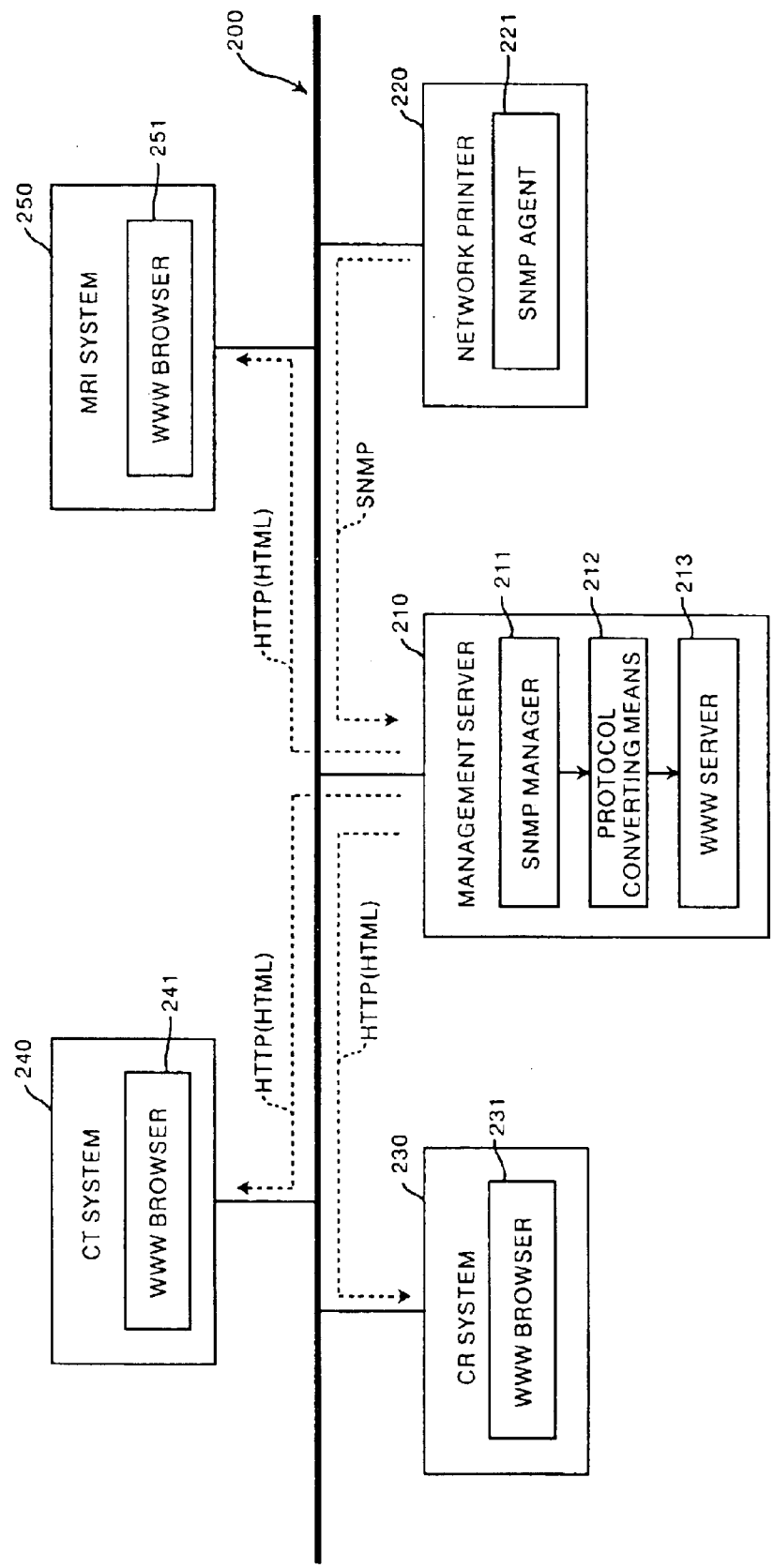
FIG. 8 is a block diagram showing an embodiment of the device for monitoring a network printer in a medical network in accordance with the present invention.

FIG. 8 is a block diagram showing an embodiment of the device for monitoring a network printer in a medical network in accordance with the present invention. With reference to FIG. 8, a medical network 200 is a network for processing medical images. The medical network 200 is connected to terminals, such as a CR system 230, a CT system 240, and an MRI system 250, which are image information input modalities. The medical network 200 is also connected to a network printer 220, which serves as an image output device. Other image information input modalities, other printers, display devices, and the like, may also be connected to the medical network 200.

The CR system 230, the CT system 240, and the MRI system 250 operate under management with different kinds of OS's. The CR system 230, the CT system 240, and the MRI system 250 serve as the terminals and can give an image output instruction to the network printer 220. In the terminals 230, 240, and 250, WWW browsers 231, 241, and 251 are respectively set up. With the WWW browsers 231, 241, and 251, information (a signal) having been described in a HyperText Markup Language (HTML) can be displayed on monitors of the terminals 230, 240, and 250.

The network printer 220 receives the output instruction via the medical network 200 from each of the terminals 230, 240, and 250 and reproduces an image according to the output instruction on film. The network printer 220 is provided with an SNMP agent 221. When a signal making a request for a state concerning output is received, the SNMP agent 221 outputs a monitor signal, which represents a state of proceeding of output and a state concerning whether expendable supplies, such as film, have or have not run out during the output, in accordance with a special-purpose protocol SNMP.

Also, a management server 210, which serves as the monitoring device for the network printer 220, is connected to the medical network 200. The management server 210 comprises an SNMP manager 211, a protocol converting means 212, and a WWW server 213. The SNMP manager 211 receives the signal, which makes a request for a state concerning output, from the medical network 200 and sends the request signal to the SNMP agent 221 of the network printer 220. Also, the SNMP manager 211 fetches the monitor signal according to the SNMP on the medical network 200. The protocol converting means 212 converts the monitor signal according to the SNMP, which has been fetched by the SNMP manager 211, into a signal (in the HTML) according to the protocol HTTP. In accordance with the signal, which makes a request for a state concerning output of the network printer 220 and is received from the terminal 230, 240, or 250, the WWW server 213 outputs the monitor signal according to the HTTP as a push type of information into the terminal 230, 240, or 250, which has made the request.

How the management server 210, which serves as the device for monitoring the network printer, operates will be described hereinbelow.

Firstly, an image output instruction is given from the CR system 230, which is one of the terminals on the medical network 200, via the medical network 200 to the network printer 220. Also, at this time, the signal, which makes a request for a state concerning output of the network printer 220, is outputted from the CR system 230. The output state requesting signal is fed via the medical network 200 into the SNMP manager 211 of the management server 210. The SNMP manager 211 feeds the received output state requesting signal into the SNMP agent 221 of the network printer 220.

The network printer 220 receives the output instruction from the CR system 230 and reproduces the image on the film in accordance with the request. Also, with respect to the output state requesting signal having been received from the SNMP manager 211, the SNMP agent 221 feeds the monitor signal, which represents the state of proceeding of output and the state concerning whether expendable supplies, such as film, have or have not run out during the output, in accordance with the special-purpose protocol SNMP into the medical network 200.

By way of example, when the network printer 220 is operating normally, the monitor signal may represent identification (ID) information concerning the image that is being reproduced, ID information concerning the terminal which has made the output request, the number of outputted sheets of film, which serves as information concerning the state of proceeding of output, the state of processing liquids, such as a developing solution and a fixing solution, the size of the film, the base color of the film, the state of a receiving magazine, and the like. When the network printer 220 runs out of the film serving as the output medium and stops, the monitor signal may represent the state of film exhaustion and the state of operation stop. When the network printer 220 stops due to exhaustion of other expendable supplies or when the film clogs in a discharging path of the network printer 220 and cannot be discharged normally, the monitor signal may represent the corresponding operation failure. Also, when the network printer 220 is not operating due to the absence of the image output instruction, the monitor signal may represent the non-operating state.

The monitor signal according to the SNMP, which has been fed to the medical network 200, is fetched by the SNMP manager 211 of the management server 210. The SNMP manager 211 feeds the fetched monitor signal into the protocol converting means 212. The protocol converting means 212 converts the received monitor signal according to the SNMP into the monitor signal in the HTML according to the HTTP and feeds the converted monitor signal into the WWW server 213.

Thereafter, in accordance with the output state requesting signal having been received via the medical network 200, the WWW server 213 feeds the monitor signal in the HTML according to the HTTP, which has been received from the protocol converting means 212, as a push type of information into the CR system 230, which has made the request for the state concerning output.

The monitor signal in the HTML, which has been fed out from the WWW server 213, is fed via the medical network 200 into the CR system 230. The CR system 230 opens the set-up WWW browser 231 and displays the monitor signal in the HTML as visible information on the monitor.

In such cases, when a signal, which makes a request for the state concerning output of the network printer 220, is fed out from one of the other terminals (e.g., the CT system 240), which has not given the image output instruction, the output state requesting signal is fed via the medical network 200 into the management server 210. With respect to the output state requesting signal, the WWW server 213 feeds the monitor signal in the HTML according to the HTTP as a push type of information into the CT system 240, which has made the request for the state concerning output. As a result, in the CT system 240, which is located at a position remote from the CR system 230 and the network printer 220, it can be found that the network printer 220 is reproducing the image in accordance with the instruction given from the CR system 230. Therefore, for example, an image output instruction can be given to the network printer 220 after the image reproduction, which is carried out in accordance with the instruction given by the CR system 230, has been finished. In this manner, the timing, with which the image output instruction is given, can be determined appropriately. Also, in cases where a plurality of printers are connected to the medical network 200, a printer which is not operating can be found from a remote position. Therefore, it is unnecessary to wait before the printer which is operating becomes free, and temporal loss can thereby be reduced.

As described above, with this embodiment of the management server 210, the state concerning output of the network printer 220 can be remote-monitored at the CR system 230, which is located at a position remote from the network printer 220, and the timing, with which the film output from the network printer 220 is finished, can be found appropriately. Therefore, considerable time and labor are not required, and an examination work can be carried out efficiently.

Also, the monitor signal is described as the HTML signal, which has a high flexibility and can be displayed with the WWW browsers utilized in the terminals 230, 240, and 250 operating under management of different OS's. Therefore, it is unnecessary for special-purpose software functions for monitoring the state of output to be provided with respect to each of various kinds of OS's of the terminals. Therefore, the network can be constructed comparatively easily and at a low cost.

An embodiment of the system for managing a parameter in accordance with the present invention will be described hereinbelow.

Figure 9:
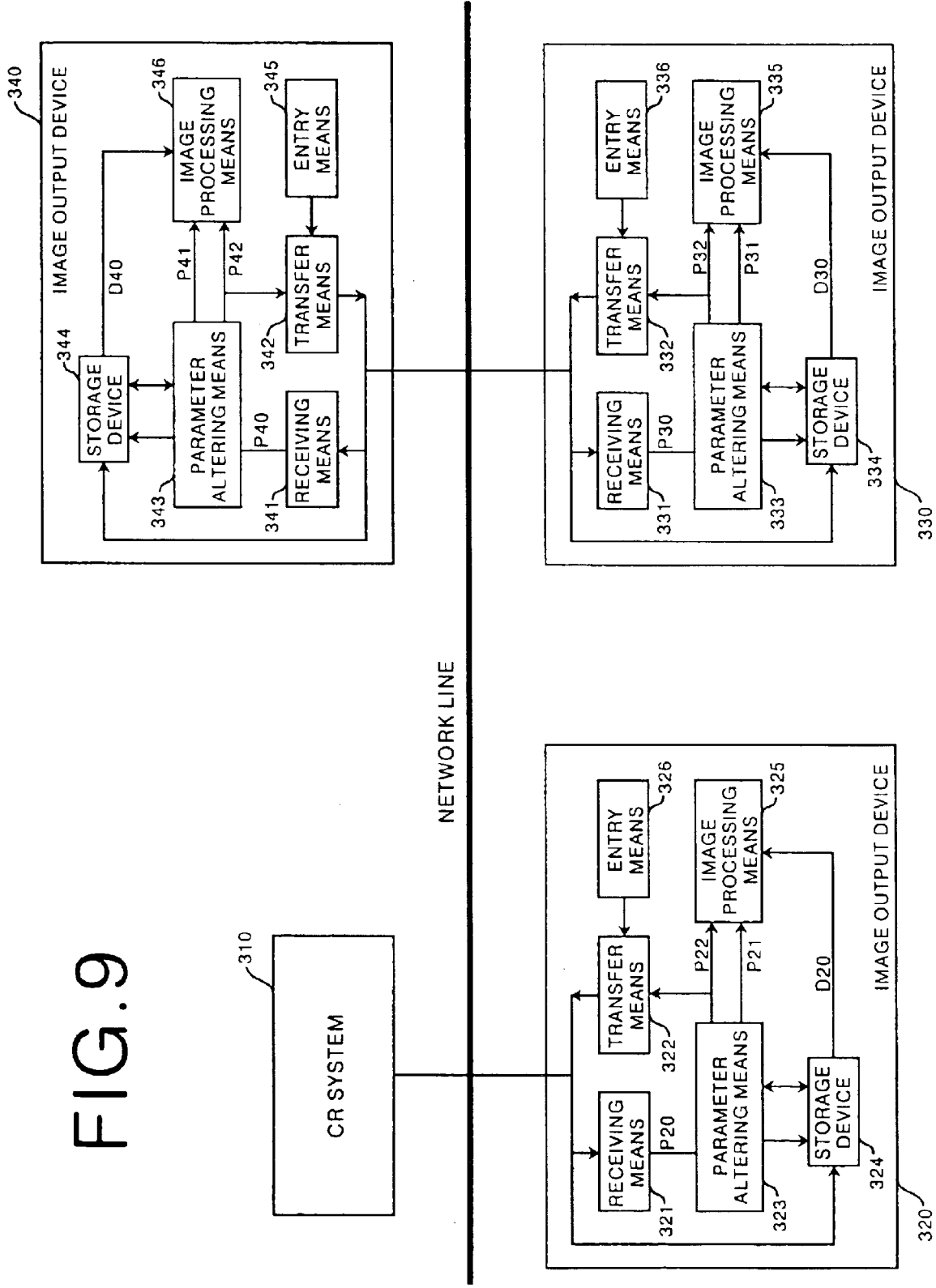
FIG. 9 is a block diagram showing an embodiment of the system for managing a parameter in accordance with the present invention.

FIG. 9 is a block diagram showing an embodiment of the system for managing a parameter in accordance with the present invention. As illustrated in FIG. 9, this embodiment of the parameter managing system comprises a CR system 310 and image output devices 320, 330, and 340. The CR system 310 records an image of an object and obtains an image signal, which represents the image. Each of the image output devices 320, 330, and 340 receives the image signal from the CR system 310, carries out predetermined image processing on the image signal, reproduces a visible image from the processing image signal, which has been obtained from the image processing, and displays the visible image on a CRT display device (not shown), or the like. The CR system 310 and the image output devices 320, 330, and 340 are connected with one another via a network line.

The image output device 320 comprises a storage device 324 for storing the image signal, which is received from the CR system 310, and information, which represents a parameter representing the conditions of the image processing having been carried out by the CR system 310. The image output device 320 also comprises a receiving means 321 for receiving the information, which represents the parameter, from each of the other image output devices 330 and 340. The image output device 320 further comprises a parameter altering means 323 for reading the information, which represents the parameter, from the storage device 324, altering the thus read parameter, and feeds the information, which represents a parameter P22 after being altered and a parameter P21 before being altered (already existing in the image output device 320), into an image processing means 325. The image output device 320 still further comprises the image processing means 325 for carrying out image processing on an image signal D20, which has been read from the storage device 324, by selectively using the parameter P21 or the parameter P22, which have been received from the parameter altering means 323. The image output device 320 also comprises a transfer means 322 for transferring the information, which represents the parameter P22 after being altered, into one of the other image output devices specified by an entry means 326. Each of the other image output devices 330 and 340 has the same constitution as that in the image output device 320. In FIG. 9, as for each of the image output devices 330 and 340, each of the elements similar to those of the image output device 320 is numbered with a reference numeral, in which the number of units is the same as that in the reference numeral of the corresponding element of the image output device 320, and the number of tens and the number of hundreds are altered to correspond to those of the reference numeral of the image output device.

How the parameter is managed in the parameter managing system will be described hereinbelow.

In the CR system 310, the image of the object is recorded, the image signal representing the image is obtained, and normalization processing and predetermined image processing are carried out on the image signal. Therefore, the normalized original image signal before being subjected to the image processing and the information, which represents the parameter representing the image processing conditions, are fed into the image output devices 320, 330, and 340. The storage devices 324, 334, and 344, which are provided respectively in the image output devices 320, 330, and 340, temporarily store the received original image signal and the information representing the parameter. Therefore, in the image output devices 320, 330, and 340, the same original image signal and the same parameter are stored. The parameter is stored as a data base so as to correspond to index information, which represents the kind of image (the image recording menu), such as the image recording system with which the image was recorded, the date of the image recording, the diagnosis department, the name of patient, the kind of examination, and the like.

In each of the image output devices 320, 330, and 340, the image processing is carried out by using the stored original image signal D20, or the like, and the parameter P21, or the like, and a visible image is displayed on the CRT display device (not shown). Also, the parameter may be altered according to preference of the operator, or the like, and image processing may be carried out under image processing conditions with the altered parameter P22, or the like. An image having thus been obtained from the image processing can be reproduced. Also, the existing parameter can be altered into an altered parameter, and the altered parameter can be stored. Such an operation corresponds to the updating of the parameter. Further, in cases where the altered parameter P22, or the like, is stored by taking an index information number different from the existing one, both of the existing parameter P21, or the like, and the altered parameter P22, or the like, can be stored.

Figure 10:
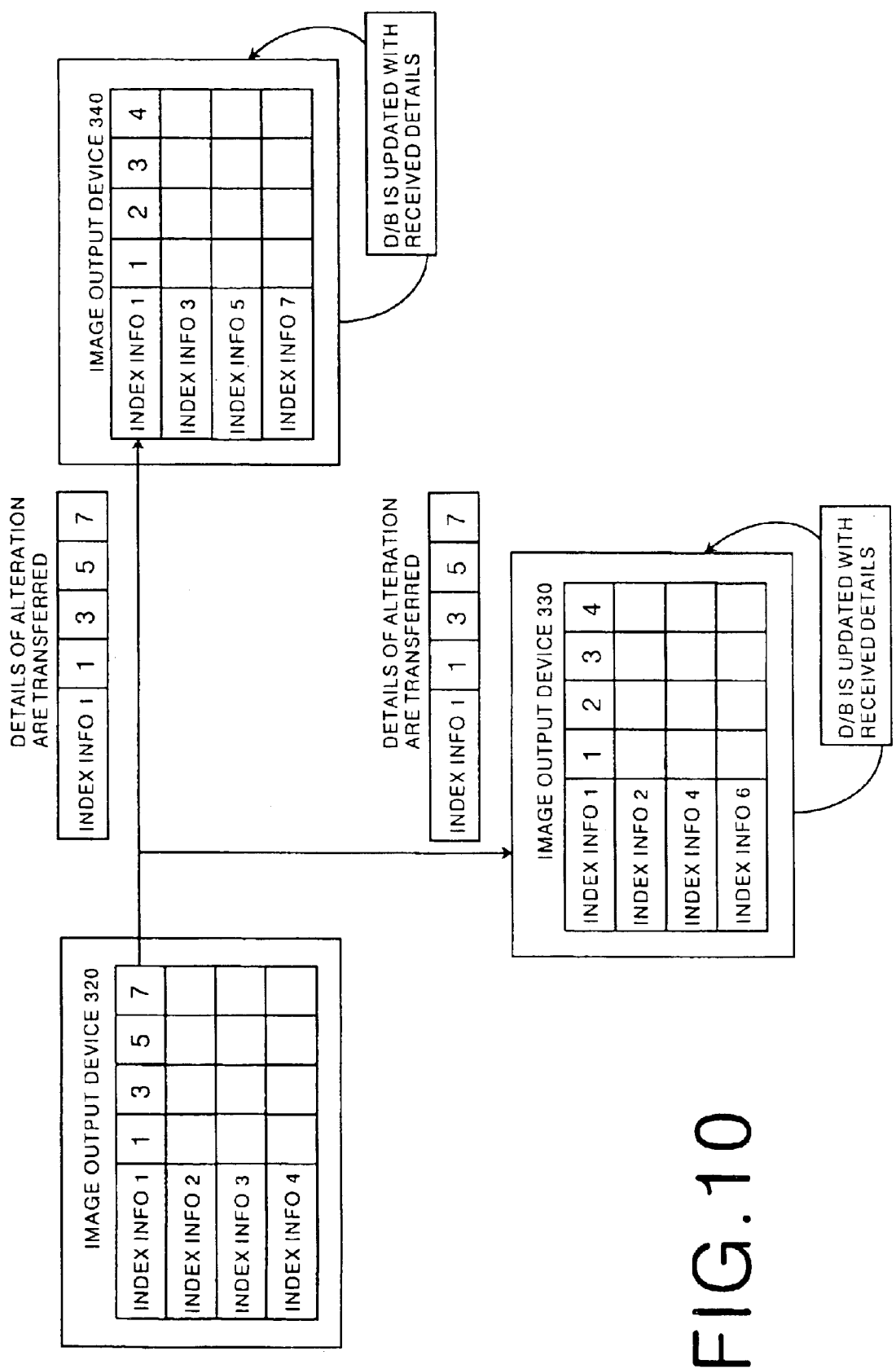
FIG. 10 is an explanatory view showing examples of parameters in the embodiment of the system for managing a parameter shown in FIG. 9.

FIG. 10 shows examples of parameters, which are stored as a data base in the storage devices 324, 334, and 344 after the image processing has been carried out by altering the parameters in the image output devices 320, 330, and 340. In the storage device 324, the parameter corresponding to each of index information 1, 2, 3, and 4 is stored. In the storage device 334, the parameter corresponding to each of index information 1, 2, 4, and 6 is stored. In the storage device 344, the parameter corresponding to each of index information 1, 3, 5, and 7 is stored. The parameter corresponding to the index information 1 of each of the storage devices 324, 334, and 344 is <1234>. In FIG. 10, the parameter corresponding to the index information 1 of the storage device 324 is illustrated as being <1357>. The parameter is the altered parameter, which will be described later. Before being altered, the parameter is <1234>. Parameters corresponding to the other pieces of index information are not shown in FIG. 10.

How the parameter corresponding to the index information 1 is altered in the image output device 320 and how the altered parameter is reflected in the image output devices 330 and 340 will be described hereinbelow.

Information (transfer destination specifying information) for specifying each of the other storage devices having the same index information as the index information, which each of the storage devices 324, 334, and 344 has, is entered previously in each of the entry means 326, 336, and 346. The transfer destination specifying information may thus be entered in each of the entry means 326, 336, and 346. Alternatively, pieces of transfer destination specifying information may be entered together in a specific device (e.g. the storage device 324) or in a different storage means (such as a server).

When the parameter is altered in the image output device 320 and the altered parameter is to be reflected in each of the other image output devices, such that the image output device, to which the information representing the altered parameter is to be transferred, may be specified, reference is firstly made to the transfer destination specifying information, which has been entered in the entry means 326. In this manner, each of the other storage devices, which has the same index information as the index information corresponding to the altered parameter, is specified.

For example, when the parameter corresponding to the index information 1 stored in the storage device 324 has been altered from <1234> to <1357>, it is specified that the storage devices having the same index information 1 are the storage devices 334 and 344. It is thereby found that the image output devices, to which the information representing the altered parameter is to be transferred, are the image output devices 330 and 340.

After the other image output devices, in which the altered parameter is to be reflected, have thus been found, the information, which represents the other image output devices, (e.g., a flag, a key code, or the like; hereinbelow referred to as the flag information) and the information, which represents the altered parameter <1357>, are fed out via the transfer means 322 to the network line.

In the image output device 330, the receiving means 331 receives the flag information and the information representing the altered parameter, which have been transferred via the network line. Also, reference is made to the flag information, and a judgment is made as to whether the received parameter is the one which has been transferred toward the image output device 330. In cases where it has been judged that the received parameter is the one which has been transferred toward the image output device 330, the storage device 334 stores the received information such that the received parameter P30 and the index information 1 can be recognized. Also, the same processing is carried out in the image output device 340. In the example described above, the altered parameter <1357> is the one corresponding to the index information 1, and the parameter <1357> is stored in both of the storage devices 334 and 344. At this time, predetermined warning or displaying may be carried out such that the operator can recognize the receiving of the parameter.

In this manner, the existing parameter is not immediately updated into the received parameter such that, in cases where the image output device having received the parameter is carrying out the image processing by using the existing parameter, the image processing may not be adversely affected by alteration of the parameter, and such that the existing parameter or the received parameter may be utilized selectively. Therefore, in cases where no problem occurs when the existing parameter is immediately updated into the received parameter, the parameter updating may be carried out automatically when the parameter is received.

In cases where the received parameter is utilized in the image output device 330 or 340, the parameter is read from the storage device 334 or 344, and the thus read parameter is fed as an altered parameter P32 or P42 of the corresponding device into the image processing means 335 or 345. The image processing means 335 carries out the image processing on the image signal D30, which has been read from the storage device 334, by selectively using the existing parameter P31 <1234> or the altered parameter P32 <1357>. In the same manner, the image processing means 345 carries out the image processing on the image signal D40, which has been read from the storage device 344, by selectively using the existing parameter P41 <1234> or the altered parameter P42 <1357>.

In the image output device 330, in cases where it has been judged that the existing parameter P31 <1234> may be altered into the altered parameter P32 <1357>, the parameter P31 <1234>, which has been stored in the data base, is altered into the altered parameter P32 <1357>. (The operation corresponds to the updating of the data base.) Alternatively, an index information number different from the index information 1 corresponding to the parameter P31 may be employed, and the altered parameter P32 <1357> may be stored in the data base so as to correspond to the newly employed index information number. In this manner, the existing parameter P31 <1234> can be kept unerased. The same processing may be carried out in the image output device 340.

In the same manner as that described above, a parameter may be altered in each of the other image output devices 330 and 340, and the information representing the altered parameter may be transferred to the image output device 320.

As described above, with this embodiment of the system for managing a parameter in accordance with the present invention, in cases where a parameter is altered in one of the image output devices, the details of the alteration can be reflected easily in all of the other image output devices or in a specific one of the other image output devices. Also, insofar as it is not judged that the transferred parameter is unnecessary, the altered parameter can be reliably reflected in all of the other image output devices or in a specific one of the other image output devices.

In the embodiment described above, reference is made to the information having been entered in the entry means, and the information representing the altered parameter is transferred to all of the image output devices, which are provided with the storage devices having the index information corresponding to the altered parameter. However, the method and system for managing a parameter in accordance with the present invention are not limited to the aforesaid embodiment, and the operation for specifying the image output device, to which the information representing the altered parameter is to be transferred, may be specified in one of various other ways. For example, the information representing the altered parameter may be transferred to only a specific image output device selected from among the image output devices having the same index information. Also, instead of the image output device, to which the information representing the altered parameter is to be transferred, being specified with the entry means, the information may be transferred in a data format, such that the altered parameter and the corresponding index information can be discriminated, equally to every device, to a device, which is located in a specific diagnosis department, or the like. On the side of the device receiving the information, reference may be made to the received index information, and the transferred parameter may be received with respect to only the parameter corresponding to the same index information as the index information which the device receiving the information has.

What is claimed is:

1. An interfacing method, wherein a plurality of network printers, which are provided with different kinds of film for image reproduction, are connected by an interface unit to a network, the method comprising the steps of, in the interface unit:

i) recognizing available kinds of film with respect to each of the network printers, which are connected to the interface unit, ii) selecting a network printer, which is among the plurality of the network printers and which corresponds to a kind of film coinciding with an output request sent via the network to the interface unit from a terminal connected to the network, in accordance with the results of said recognition, and iii) giving an output instruction, which coincides with said output request, to the thus selected network printer.

2. The interface unit as defined in claim 1, wherein the selection of a network printer based on the output request is automated.

3. The method of claim 1, wherein at least one modality is connected to the network and the selected network printer receives image data from the at least one modality via the network and prints the image data when the selected printer receives the output instruction.

4. An interfacing method as defined in claim 1 wherein, in cases where there is no network printer, which corresponds to the kind of film coinciding with said output request, a network printer, which corresponds to the kind of film closest to the kind of film coinciding with said output request, is selected as the network printer, which corresponds to the kind of film coinciding with said output request, and an output instruction, which specifies said closest kind of film, is given as said output instruction, which coincides with said output request, to the thus selected network printer.

5. The interface unit as defined in claim 4, wherein the selection of a network printer based on the output request is automated.

6. An interfacing method, wherein at least one network printer among a plurality of network printers, which are provided with different kinds of film for image reproduction, is connected by at least one of at least one of a first interface unit and at least one of a second interface unit to a network, the method comprising in the first interface unit:

receiving printer information from the second interface unit;

recognizing available kinds of film with respect to each of the at least one network printer, which is connected to the first interface unit;

selecting a network printer, which is among the plurality of the network printers and which corresponds to a kind of film coinciding with an output request sent via the network to the first interface unit from a terminal connected to the network, in accordance with results of said recognition in the first interface unit and the printer information received from the second interface unit;

sending an output instruction to the selected network printer if the selected network printer is connected to the first interface unit, and sending the output instruction to the second interface unit if the selected printer is connected to the second interface unit; and the method comprising in the second interface unit:

recognizing available kinds of film with respect to each of the at least one network printer, which is connected to the second interface unit;

receiving the output instruction from the first interface unit;

sending the output instruction to the selected network printer; and sending results of said recognition in the second interface unit to the first interface unit as the printer information.

7. An interfacing method as defined in claim 6 wherein, in cases where there is no network printer, which corresponds to the kind of film coinciding with said output request, a network printer, which corresponds to the kind of film closest to the kind of film coinciding with said output request, is selected as the network printer, which corresponds to the kind of film coinciding with said output request, and an output instruction, which specifies said closest kind of film, is given as said output instruction, which coincides with said output request, to the selected network printer.

8. The interface unit as defined in claim 6, wherein the selection of a network printer based on the output request is automated.

9. The method of claim 6, wherein at least one modality is connected to the network and the selected network printer receives image data from the at least one modality via the network and prints the image data when the selected printer receives the output instruction.

10. An interfacing method as defined in any of claims 1, 4, 6 or 7 wherein, in cases where each of the network printers connected to the interface unit is designed to send a monitor signal, which represents a state concerning output, in accordance with a special-purpose protocol, and each of a plurality of terminals, which constitute the network, is provided with general-purpose displaying software functions and operates under management with one of plural kinds of operating systems having different forms, said monitor signal having been sent in accordance with said special-purpose protocol is converted into a signal according to a protocol, which is adapted to displaying with said displaying software functions.

11. An interfacing method as defined in claim 10 wherein said special-purpose protocol is a Simple Network Management Protocol, said displaying software functions is a World Wide Web browser, and said protocol adapted to displaying with said displaying software functions is a HyperText Transfer Protocol.

12. The interface unit as defined in claim 7, wherein the selection of a network printer based on the output request is automated.

13. An interface unit for connecting a plurality of network printers, which are provided with different kinds of film for image reproduction, to a network, the interface unit comprising:

i) a film kind recognizing means for recognizing available kinds of film with respect to each of the network printers, which are connected to the interface unit, and ii) a printer selecting means for selecting a network printer, which is among the plurality of the network printers and which corresponds to a kind of film coinciding with an output request sent via the network to the interface unit from a terminal connected to the network, in accordance with the results of said recognition having been carried out by said film kind recognizing means, wherein an output instruction, which coincides with said output request, is given to the network printer having been selected by said printer selecting means.

14. An interface unit as defined in claim 13 wherein, in cases where there is no network printer, which corresponds to the kind of film coinciding with said output request, said printer selecting means selects a network printer, which corresponds to the kind of film closest to the kind of film coinciding with said output request, as the network printer, which corresponds to the kind of film coinciding with said output request, and an output instruction, which specifies said closest kind of film, is given as said output instruction, which coincides with said output request, to the network printer having been selected by said printer selecting means.

15. The interface unit as defined in claim 13, wherein the kind of film is defined by a film size.

16. The interface unit as defined in claim 14, wherein the kind of film is defined by a film size.

17. The interface unit as defined in claim 13, wherein the kind of film is defined by a film base color.

18. The interface unit as defined in claim 14, wherein the kind of film is defined by a film base color.

19. The interface unit as defined in claim 13, wherein the selection of a network printer based on the output request is automated.

20. The interface unit as defined in claim 14, wherein the selection of a network printer based on the output request is automated.

21. The interface unit of claim 13, wherein at least one modality is connected to the network and the selected network printer receives image data from the at least one modality via the network and prints the image data when the selected printer receives the output instruction.

22. An interface unit, comprising:

at least one of a first interface unit and at least one of a second interface unit, wherein at least one of the first interface unit and second interface unit connects at least one network printer among a plurality of network printers, which are provided with different kinds of film for image reproduction, to a network, wherein the first interface unit comprises a first receiving means for receiving printer information from the second interface unit;

a first film kind recognizing means for recognizing available kinds of film with respect to each of the at least one network printer, which is connected to the first interface unit;

a printer selecting means for selecting a network printer, which is among the plurality of the network printers and which corresponds to a kind of film coinciding with an output request sent via the network to the first interface unit from a terminal connected to the network, in accordance with results from the first film kind recognizing means and the printer information received from the second interface unit; and an first output sending means for sending an output instruction to the selected network printer if the selected network printer is connected to the first interface unit and sending the output instruction to the second interface unit if the selected printer is connected to the second interface unit; and wherein the second interface unit comprises a second film kind recognizing means for recognizing available kinds of film with respect to each of the at least one network printer, which is connected to the second interface unit;

a second receiving means for receiving the output instruction from the first interface unit;

a second output sending means for sending the output instruction to the selected network printer; and an information sending means for sending results from the second film kind recognizing means to the first information unit as the printer information.

23. An interface unit as defined in claim 22 wherein, in cases where there is no network printer, which corresponds to the kind of film coinciding with said output request, said printer selecting means selects a network printer, which corresponds to the kind of film closest to the kind of film coinciding with said output request, as the network printer, which corresponds to the kind of film coinciding with said output request, and an output instruction, which specifies said closest kind of film, is given as said output instruction, which coincides with said output request, to the selected network printer.

24. An interface unit as defined in any of claims 13, 14, 22 or 23 wherein, in cases where each of the network printers connected to the interface unit is designed to send a monitor signal, which represents a state concerning output, in accordance with a special-purpose protocol, and each of a plurality of terminals, which constitute the network, is provided with general-purpose displaying software functions and operates under management with one of plural kinds of operating systems having different forms, the interface unit further comprises a protocol converting means for converting said monitor signal, which has been sent in accordance with said special-purpose protocol, into a signal according to a protocol, which is adapted to displaying with said displaying software functions.

25. An interface unit as defined in claim 24 wherein said special-purpose protocol is a Simple Network Management Protocol, said displaying software functions is a World Wide Web browser, and said protocol adapted to displaying with said displaying software functions is a HyperText Transfer Protocol.

26. A client apparatus, which is provided with the functions of an interface unit as defined in any of claims 13, 14, 22 or 23.

27. The interface unit as defined in claim 22, wherein the kind of film is defined by a film size.

28. The interface unit as defined in claim 23, wherein the kind of film is defined by a film size.

29. The interface unit as defined in claim 22, wherein the kind of film is defined by a film base color.

30. The interface unit as defined in claim 23, wherein the kind of film is defined by a film base color.

31. The interface unit as defined in claim 22, wherein the selection of a network printer based on the output request is automated.

32. The interface unit as defined in claim 23, wherein the selection of a network printer based on the output request is automated.

33. The interface unit of claim 22, wherein at least one modality is connected to the network and the selected network printer receives image data from the at least one modality via the network and prints the image data when the selected printer receives the output instruction.

* * * * *